US012274821B2

(12) United States Patent
Knoll et al.

(10) Patent No.: US 12,274,821 B2
(45) Date of Patent: *Apr. 15, 2025

(54) OXYGENATOR

(71) Applicant: Medtronic, Inc., Minneapolis, MN (US)

(72) Inventors: John Knoll, Minneapolis, MN (US); Neil Nye, Minneapolis, MN (US); Brian Steffens, Minneapolis, MN (US); Michael Van Driel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 830 days.

This patent is subject to a terminal disclaimer.

(21) Appl. No.: 17/497,371

(22) Filed: Oct. 8, 2021

(65) Prior Publication Data

US 2022/0023520 A1 Jan. 27, 2022

Related U.S. Application Data

(63) Continuation of application No. 16/170,390, filed on Oct. 25, 2018, now Pat. No. 11,141,517.

(51) Int. Cl.
*A61M 1/16* (2006.01)
*A61M 1/36* (2006.01)
(Continued)

(52) U.S. Cl.
CPC ........ *A61M 1/1698* (2013.01); *A61M 1/1629* (2014.02); *A61M 1/3623* (2022.05);
(Continued)

(58) Field of Classification Search
CPC .............. A61M 1/1698; A61M 1/1623; A61M 1/1625; A61M 1/1627; A61M 1/1629; A61M 1/3638; A61M 1/3623; A61M 1/3627; A61M 2202/0225; B01D 63/04; B01D 63/043; B01D 63/046; B01D 71/26
See application file for complete search history.

(56) References Cited

U.S. PATENT DOCUMENTS 8,133,195 B2 3/2012 Blicke et al.
8,318,092 B2 11/2012 Reggiani et al.
(Continued)

*Primary Examiner* — Philip R Wiest
(74) *Attorney, Agent, or Firm* — Michael Best & Friedrich LLP

(57) ABSTRACT

An oxygenator apparatus for use in an extracorporeal circuit. The apparatus includes a housing and a membrane assembly disposed within the housing. The membrane assembly includes a first plurality of gas exchange elements disposed in a first zone and a second plurality of gas exchange elements disposed in a second zone. The second zone is arranged concentrically around the first zone. The first and second plurality of gas exchange elements are fluidly open along a body and fluidly separated along a distal end. The first zone is configured to be fluidly coupled to an oxygen source and the second zone is configured to be fluidly coupled to a negative pressure source. A blood flow path includes a generally radial flow through the first zone to add oxygen to the blood and the second zone to separate gaseous micro emboli from the blood through the plurality of gas exchange elements.

17 Claims, 5 Drawing Sheets

(51) Int. Cl.
  *B01D 63/04* (2006.01)
  *B01D 71/26* (2006.01)
(52) U.S. Cl.
  CPC ........ *A61M 1/3627* (2013.01); *A61M 1/3638* (2014.02); *B01D 63/04* (2013.01); *B01D 71/261* (2022.08); *A61M 2202/0225* (2013.01)

(56) References Cited

U.S. PATENT DOCUMENTS

| | | |
|---|---|---|
| 8,518,259 B2 | 8/2013 | Cloutier et al. |
| 8,545,754 B2 | 10/2013 | Carpenter et al. |
| 8,685,320 B2 | 4/2014 | Ogihara et al. |
| 8,795,591 B2 | 8/2014 | Roller et al. |
| 8,968,652 B2 | 3/2015 | Ogihara |
| 9,199,025 B2 | 12/2015 | Mizoguchi et al. |
| 11,141,517 B2 * | 10/2021 | Knoll .................. A61M 1/3623 |
| 2010/0269342 A1 * | 10/2010 | Carpenter .......... B01D 63/0233 29/890.03 |
| 2014/0030149 A1 * | 1/2014 | Takeuchi ............ A61M 1/3623 422/48 |
| 2016/0015881 A1 | 1/2016 | Utsugida et al. |
| 2017/0087293 A1 | 3/2017 | Gloss et al. |

\* cited by examiner

OXYGENATOR

CROSS-REFERENCE TO RELATED APPLICATIONS

This Patent Application is a Continuation of U.S. patent application Ser. No. 16/170,390, entitled OXYGENATOR, filed Oct. 25, 2018 of which is incorporated herein by reference.

FIELD

The present technology is generally related to oxygenating blood in an extracorporeal blood circuit. More particularly, the present disclosure relates to systems and methods for optimizing removal of gaseous micro emboli from a patient's blood through an oxygenator operating in an extracorporeal blood circuit.

BACKGROUND

An extracorporeal blood circuit is commonly used during cardiopulmonary bypass to withdraw blood from the venous portion of the patient's circulation system (via a venous cannula) and return the blood to the arterial portion (via an arterial cannula). The extracorporeal blood circuit typically includes a venous drainage line, a venous blood reservoir, a blood pump, an oxygenator, a heat exchanger, one or more filters, and blood transporting tubing, ports, and connection pieces interconnecting the components.

Blood oxygenators are disposable components of extracorporeal circuits and are used to oxygenate blood. In general terms, the oxygenator takes over, either partially or completely, the normal gas exchange function of the patient's lungs. The oxygenator conventionally employs a microporous membrane or bundle comprised of thousands of microporous or semipermeable hollow fibers. Blood flow is directed around the outside surfaces of the hollow fibers. Concurrently, an oxygen-rich gas mixture is passed through the fiber lumens. The hollow fibers are considered to form a membrane, separating the "gas side" from the "blood side" pathway of the oxygenator with the wall of the hollow fiber separating the gas side from the blood side. Due to the relatively high concentration of carbon dioxide in the blood arriving from the patient, carbon dioxide is transferred from the blood, diffusing across the microporous fibers and into the passing stream of oxygenating gas. At the same time, oxygen is transferred from the oxygenating gas, diffusing across the fibers and into the blood. The oxygen content of the blood is thereby raised, and the carbon dioxide content is reduced.

Conventionally, a filter device (e.g., an arterial filter) is be fluidly connected within the extracorporeal circuit downstream from (or upstream of) the oxygenator, and operates to remove gross air (e.g., air bubbles) and particles on the order of 18-45 microns, as well as trap gaseous micro air or micro bubbles, sometimes referred to as gaseous microemboli (GME). Arterial blood filters can incorporate a membrane or screen filter media with a sufficiently small porosity for capturing GME. The oxygenator and arterial filter devices normally are physically separated components or devices of the circuit.

Maximizing removal of Gaseous Micro Emboli (GME) from the patient's blood is considered beneficial by reducing potential harms resulting from delivery of emboli to the patient. Considerations for maximizing GME removal is limited by the physiological considerations required for gas transfer to the patient through the hollow fibers.

SUMMARY

Some aspects in accordance with principles of the present disclosure relate to an oxygenator apparatus for use in an extracorporeal circuit. The apparatus includes a housing and a membrane assembly. The housing has a blood inlet, a blood outlet, and a blood flow path from the blood inlet to the blood outlet. The housing defines a central axis and a series of zones concentrically disposed around the central axis. The membrane assembly is disposed within the housing. The membrane assembly includes a first plurality of gas exchange elements disposed in a first zone of the housing and a second plurality of gas exchange elements disposed in a second zone of the housing. The second zone is arranged concentrically around the first zone and the zones are fluidly open to one another along a body of the plurality of gas exchange elements and fluidly separated from one another along a distal end. Each of the plurality of gas exchange elements including an interior gas side and an exterior blood side. The first zone is configured to be fluidly coupled to an oxygen source to supply oxygen flow within the interior gas side of the first plurality of gas exchange elements of the first zone and the second zone is configured to be fluidly coupled to a negative pressure source to apply negative pressure to the interior side of the second plurality of gas exchange elements in the second zone. The blood flow path includes a generally radial flow through the first zone and the second zone, the first zone to add oxygen to the blood and remove carbon dioxide from the blood, and the second zone to separate gaseous micro emboli from the blood through the plurality of gas exchange elements.

Other aspects in accordance with principles of the present disclosure relate to a method of oxygenating blood and removing gaseous micro emboli within an extracorporeal blood circuit. The method includes delivering blood from a patient to an oxygenator apparatus. The oxygenator apparatus includes a housing and a membrane assembly disposed within the housing. The housing includes a blood inlet and a blood outlet. The housing defines a central axis and a series of zones fluidly open to one another and concentrically disposed around the central axis. The membrane assembly includes a plurality of gas exchange elements forming a first zone arranged around the central axis and a second zone arranged around the first zone. Each of the plurality of gas exchange elements includes an exterior surface and an interior lumen formed by an interior surface. The interior lumens of the plurality of gas exchange elements in the first zone are fluidly coupled to an oxygenation source. The interior lumens of the plurality of gas exchange elements in the second zone are fluidly coupled to a negative pressure source. The method includes directing blood from the blood inlet to the blood outlet along a blood flow path, oxygenating the blood and removing carbon dioxide from the blood as the blood flows radially through and around the plurality of gas exchange elements in the first zone, applying a negative pressure to an interior lumen of the plurality of gas exchange elements in the second zone, filtering gaseous micro emboli from the blood into the interior of at least one of the second plurality of elements, and removing the blood from the apparatus via the blood outlet.

Other aspects in accordance with principles of the present disclosure relate to a system for treating blood in an extracorporeal circuit. The system includes an oxygenator apparatus, an oxygen source, and a negative pressure source. The oxygenator apparatus includes a housing having a blood inlet and a blood outlet. The housing defining a central axis and a series of zones fluidly open to one another and concentrically disposed around the central axis. The oxygenator apparatus includes a core disposed along the central axis of the housing, the core configured to receive blood from a patient through the blood inlet, a first zone including a first plurality of gas exchange elements arranged around the core, and a second zone including a second plurality of filter elements arranged around the first plurality of gas exchange elements. The oxygen source is fluidly coupled to the first plurality of filter elements at the first zone to supply oxygen to interior lumens of the first plurality of filter elements. The negative pressure source is fluidly coupled to the second plurality of filter elements at the second zone to provide suction to interior lumens of the second plurality of filter elements. The oxygenator apparatus establishes a blood flow path from the blood inlet to the blood outlet, including generally radial flow to add oxygen to the blood and remove carbon dioxide from the blood at the first plurality of gas exchange elements and separate gaseous micro emboli from the blood at the second plurality of filter elements.

DETAILED DESCRIPTION

Figure 1A:
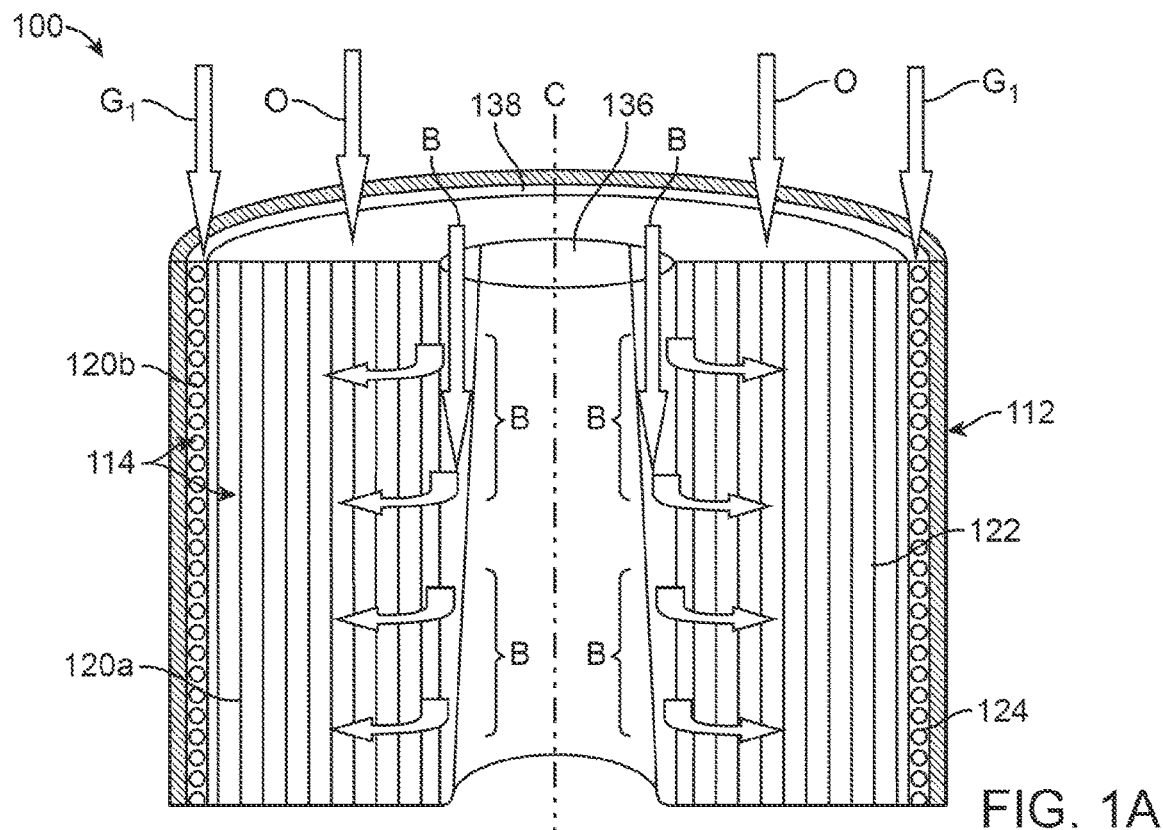
FIGS. 1A and 1B are a schematic cross-sectional views of example oxygenator apparatuses in accordance with aspects of the present disclosure.

An oxygenator apparatus 100 for use in an extracorporeal blood circuit in accordance with aspects of the present disclosure is illustrated in the partially cross-sectional view of FIG. 1A. The oxygenator apparatus 100 includes a housing 112 and a membrane assembly 114. The housing 112 defines a central axis "C" and a series of zones fluidly open to one another and concentrically disposed around the central axis "C". The membrane assembly 114 is disposed within the housing 112. The membrane assembly 114 includes a plurality of gas exchange elements 120 disposed in and forming a first zone 122 and a second zone 124. The first and second zones 122, 124 of the membrane assembly 114 may be considered as dividing a volume within the housing 112. The first zone 122 is arranged around the central axis "C" and the second zone 124 is arranged around the first zone 122, as discussed further below.

The membrane assembly 114 includes a first plurality or bundle of gas exchange elements 120a forming the first zone 122 and a second plurality or bundle of gas exchange elements 120b forming the second zone 124 within the housing 112. The first zone 122 can be an oxygenation zone and the second zone 124 can be a gaseous micro emboli (GME) removal zone, although both oxygenation can be supplied to, and GME removed from, either of both of the first and second zones 122, 124. The second, or gaseous micro emboli removal, zone 124 is arranged concentrically around the first, or oxygenation, zone 122. The first zone 122 and the second zone 124 are fluidly open to one another along a body of the plurality of gas exchange elements 120 of the membrane assembly 114. The first and second plurality of gas exchange elements 120a, 120b can extend co-axially along the central axis "C" of the housing 112, extending from a first, proximal, end to an opposing second, distal, end of the housing 112 (not shown).

The bundle or plurality of hollow tube fiber gas exchange elements 120 of the membrane assembly 114 are used for gas exchange and made of semi-permeable membranes including micropores. In some embodiments, the gas exchange elements 120 are hollow polypropylene fibers, but other materials are also acceptable. Any suitable microporous fiber can be used as the gas exchange elements 120 of the oxygenator. The gas exchange elements 120 can have an interior lumen formed by an interior surface of a fiber wall and an exterior surface (not shown). In some embodiments, the first and second plurality of gas exchange elements 120a, 120b are formed of the same fibrous bodies. In some embodiments, the first plurality of gas exchange elements 120a is a first type of fibrous body, or membrane, and the second plurality of gas exchange elements 120b is a second type of fibrous body, or membrane.

The partial cross-sectional view of the oxygenator apparatus 100 of FIG. 1A illustrates an example of how blood can flow through the oxygenator apparatus 100. In general terms, a blood flow path (indicated by arrows "B") is established from the blood inlet to the blood outlet (not shown). The blood flow path "B" may be generally longitudinally along the central axis "C" from the blood inlet and flow radial through a chamber 138 of the oxygenator apparatus 100 including the first and second zones 122, 124. The first zone 122 is fluidly open to the second zone 124 within the chamber 138, with the first zone 122 having an enlarged volume as compared to that of the second zone 124. The cylindrical shape establishes the central axis "C" of the housing 112 extending through the chamber 138. Blood flow path "B" flows around and past the hollow fibers of the first plurality of gas exchange elements 120a in the first zone 122 and then of the second plurality of gas exchange elements 120b in the second zone 124 to the blood outlet (not shown).

As the blood flow "B" moves through and around the first plurality of gas exchange elements 120a in the first zone 122, oxygen-containing gas medium flows through the interior (gas) side of the gas exchange elements 120a, as indicated by arrows "O", adding oxygen to and removing carbon-dioxide from the blood. An oxygen-containing gas medium is provided to flow through the interior (gas) side of the gas exchange elements 120 to permeate the fibers of at least the first zone 122. Oxygen may diffuse through the hollow fibers into the blood while carbon dioxide may diffuse into the hollow fibers and be removed, or separated out of the blood. Carbon dioxide from the blood surrounding the fibers diffuses through the walls of the fibers and into the gas mixture. Similarly, oxygen from the gas mixture inside the fibers diffuses through the micropores into the blood.

The gas mixture then has an elevated carbon dioxide content and preferably exits the opposite ends of the fibers as it moves out of the apparatus via a gas outlet. Other gases may also be transferred in addition to the oxygen and carbon dioxide exchanged. For example, an anesthetic gas can be included in the oxygen-containing gas medium to be infused into the blood.

The proximity of the blood and oxygen facilitates gas transfer through micropores in the fiber wall of the gas exchange elements 120a via differences in partial pressures. The rate of gas transfer is dependent upon partial pressure differences between the gas side and the blood side of the fiber membrane. Operating parameter inputs that impact partial pressure differences are limited by gas transfer considerations driven by patient physiological demand. Some of the inputs include gas sweep or flow rate through the fibers, and the percentage of pure oxygen/ambient air that is blended together and fed in the gas pathway of the fibers. Other inputs can also impact partial pressure differences. After the blood has flowed around the fibers of the bundle of gas exchange elements 120a, the blood is routed to a second plurality of gas exchange fiber elements 120b.

As the blood flow "B" continues to move radially through and around the second plurality of gas exchange elements 120b in the second zone 124. Negative pressure is applied to the "gas" side of the plurality of gas exchange elements 120b to pull GME from the blood into the "gas" side of the plurality of gas exchange elements, as indicated by arrows "$G_1$," or "$G_2$,", illustrated in FIGS. 1A and 1B, respectively. The second plurality of gas exchange elements 120b can be fluidly coupled to a negative pressure source at one of either the distal or proximal end of the second plurality of gas exchange elements 120b forming the second zone 124. Gas transfer including gaseous micro emboli can occur upon partial pressure differences between the gas side and the blood side of the fiber membranes of the second plurality of gas exchange elements 120b, with the interior gas side having a lower pressure than the blood side. The second plurality of gas exchange elements 120b of the second zone 124 can be provided an oxygen-contain gas medium, or can be provided another source of gas medium, or open to atmosphere at the end (i.e., proximal or distal end) opposite of the negative pressure source. In some embodiments, the ends of the second plurality of gas exchange elements 120b in the second zone 124 opposite of the end the negative pressure source is applied to are fluidly closed. In one embodiment, negative pressure can be selectively applied to the one end of the second plurality of gas exchange elements 120b of zone 124 independent of the gas flow, pressure and other inputs to the first plurality of gas exchange fibers to optimize GME removal from the blood without gas exchange consideration limitations of the first plurality 120a because the first zone 122 is isolated, or essentially isolated, from the negative pressure source.

The gas pathway zones indicated by arrows "O" and "G" for oxygen gas transfer "O" and GME removal "G", respectively, can be separate and independent from one another. The fluid flows (e.g., indicated by arrows "G" and "O") through the apparatus 100 can be maintained separately and compartmentalized to increase effectiveness and efficiency of both oxygenation of the blood and removal of the GME from the blood in the oxygenator apparatus 100. After the blood has flowed around the fibers of the bundle of gas exchange elements 120a and 120b it is routed outside the oxygenator housing 112 via a blood outlet port.

The membrane assembly 114 is disposed around the central axis "C". In some embodiments, the plurality of gas exchange elements 120 of the oxygenating first zone 122 can be wound onto or around a volume displacing core 136 or other centrally disposed body suitable for attachment and winding of the gas exchange elements. In some embodiments, the first and second plurality of gas exchange elements 120a, 120b are disposed helically extending in a single direction. In some embodiments, the first plurality of gas exchange elements 120a disposed helically around the central axis "C" in a first direction and the second plurality of filter elements 120b are disposed helically around the first plurality of gas exchange elements 120a in a second direction opposite the first direction. The plurality of gas exchange elements 120 can be disposed in any suitable manner within and forming the first and second zones 122, 124.

Figure 1B:
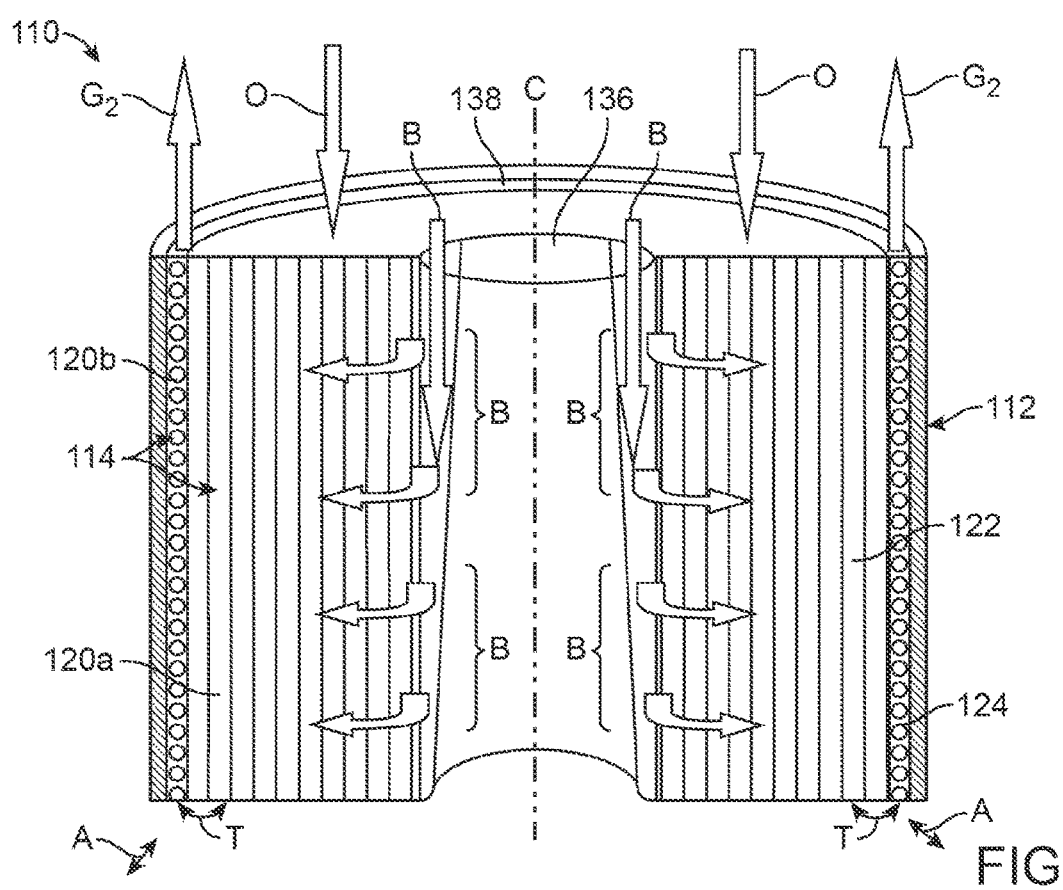

The oxygenator apparatus 110 illustrated in FIG. 1B is similar to FIG. 1A. In the embodiment of FIG. 1B, the blood flow "B" moves radially through and around the first plurality of gas exchange elements 120a in the first zone 122 and the second plurality of gas exchange elements 120b in the second zone 124. As the blood flow "B" moves through and around the plurality of gas exchange elements 120a, an oxygen-containing gas medium flows through the interior (gas) side of the gas exchange elements 120a, as indicated by arrows "O", permeating the fibers of the gas exchange elements 120a to add oxygen to and remove carbon-dioxide from the blood. After the oxygen-containing gas medium flows through and exits out of the ends of the first plurality of gas exchange elements 120a, the flow "T" transitions into the ends of and through the second plurality of gas exchange elements 120b, as pulled by a negative pressure source indicated by flow "$G_2$". The transition flow "T" may be opposite the initial flow "O". In one embodiment, ventilation to atmosphere may be provided at the transition between the first plurality of gas exchange elements 120a in the first zone 122 and the second plurality of gas exchange elements 120b in the second zone 124 as indicated by arrows "A". Ventilation to atmosphere can assist with maintaining pressure and eliminating positive pressure build up in the first zone 122. The housing 112 includes inlets, outlets, and ventilation ports as appropriate.

As illustrated in the example embodiments illustrated in FIGS. 2-5, the apparatuses of the present disclosure can combine various components of extracorporeal blood circulation into one housing. Treatment and flow of blood within the apparatuses is reflected in FIGS. 2-5. Various aspects of the oxygenator apparatuses of FIGS. 2-5 are similar to those of the oxygenator apparatus 100 described above. In general terms, a blood flow path (indicated by arrows "B") is established from the blood inlet to the blood outlet of the oxygenator apparatuses, including through cross-sections of first, or oxygenating, zones and second, or GME removal zones as well as through and/or around other various components including in the oxygenator apparatuses. As discussed further below, in some embodiments, the gas exchange elements (or fibers) of the oxygenating membrane assembly can be wound directly on a core, a heat exchanger, or other centrally disposed body suitable for attachment and winding of the gas exchange elements.

Figure 2A:
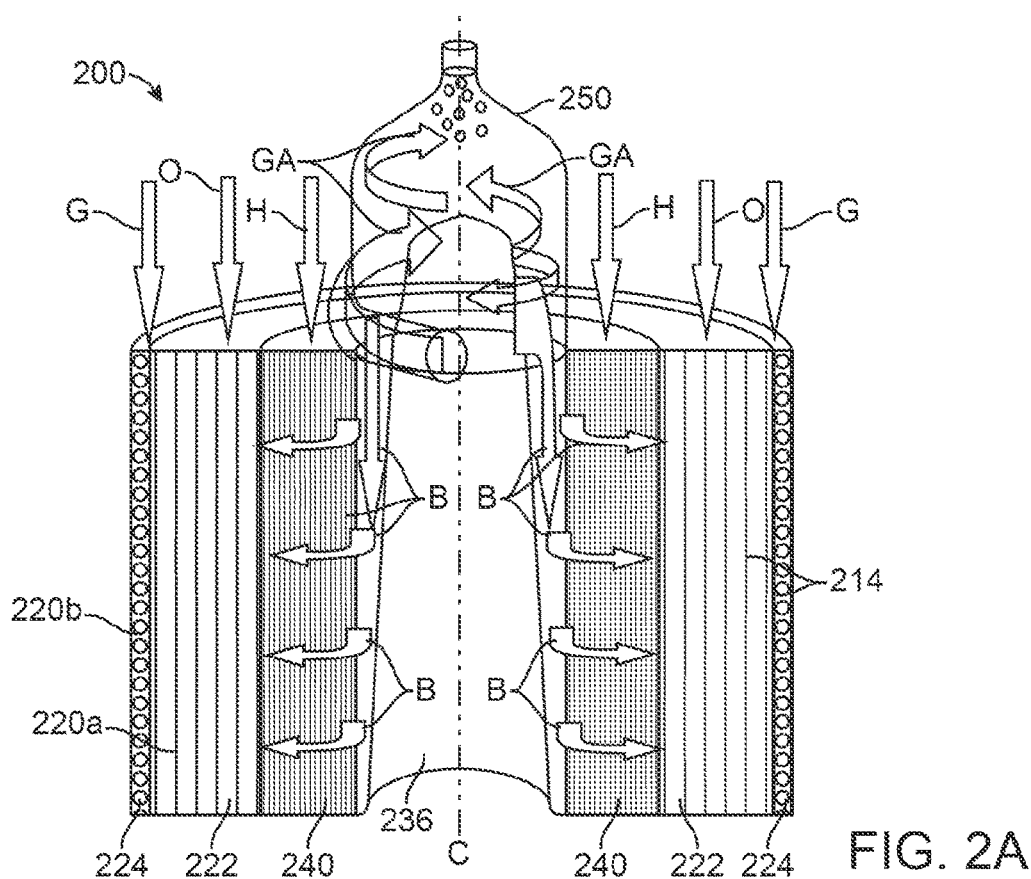
FIG. 2A a schematic cross-sectional view of another example oxygenator apparatus in accordance with aspects of the present disclosure.

In one example embodiment illustrated in FIG. 2A, a portion of the oxygenator apparatus 200 (e.g., an upper end cap shown in FIG. 5 and described below) and the central portion combine to form a de-aering region or bubble trap 250. A blood inlet (not shown) is arranged relative to the de-aering region 250 so as to direct incoming blood tangentially into the de-aering region 250. A blood outlet (not shown) is positioned downstream of a heat exchanger 240 and the oxygenating membrane assembly 214. A blood flow path, indicated with arrows "B", is defined from the blood inlet to the blood outlet, with gross air removal, indicated by arrows "GA" occurring within the de-aering region 250, and prior to interaction of the blood with the heat exchanger 240 or the oxygenating and GME removing membrane assembly 214.

Figure 2B:
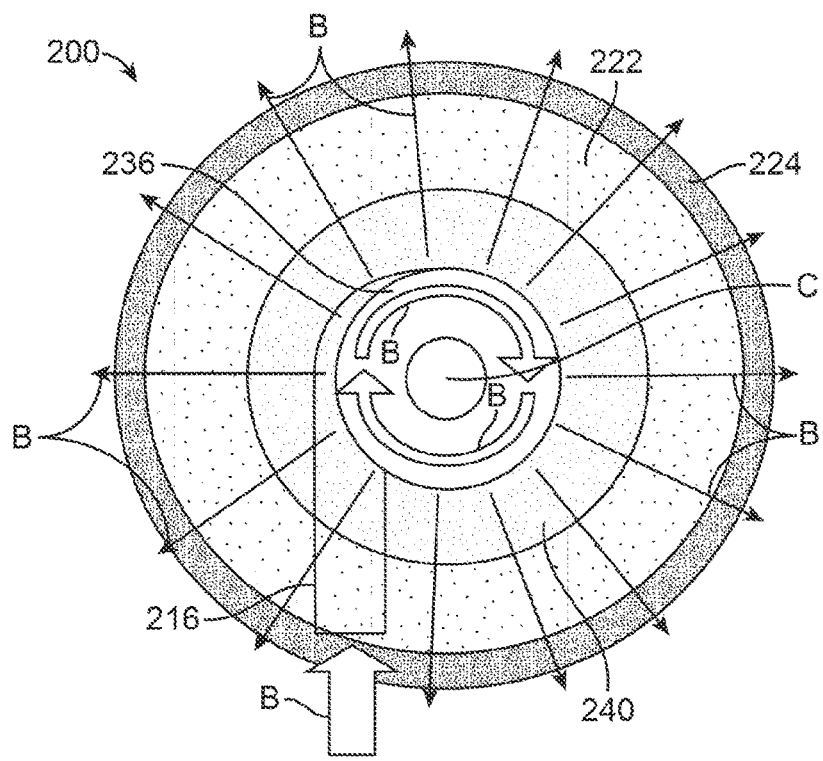
FIG. 2B a schematic cross-sectional view of the oxygenator apparatus of FIG. 2A, viewed perpendicular to the cross-sectional view of FIG. 2A, in accordance with aspects of the present disclosure.

The embodiment illustrated in the cross-sectionals views of FIGS. 2A and 2B includes the heat exchanger 240 integrated within an oxygenator apparatus 200. The heat exchanger 240 can be disposed in a zone concentrically about the central axis "C" and, in some embodiments, a central displacement core 236 disposed along the central axis "C". The membrane assembly 214 can be disposed concentrically about the heat exchanger 240. The heat exchanger 240 is generally made of a metal or plastic that is able to transfer heat effectively to blood coming into contact with the metal or plastic. With extracorporeal blood circuit applications, the heat exchanger 240 is normally formed by a series or bundle of capillary tubes. The oxygenating membrane assembly 214 can be disposed directly over the capillary tubes of the heat exchanger 240.

A suitable heat transfer fluid, such as water, is pumped through the capillary tubes of the heat exchanger 240, separate from the blood but in heat transfer relationship therewith. The heat transfer fluid flow path, indicated by arrows "H", is either heated or cooled externally of the oxygenator apparatus 200 and the heat exchanger 240 disposed within. The heat exchanger 240 functions to control or adjust a temperature of the blood in a desired direction as the blood flows around and past the hollow fibers of the heat exchanger 240. Typically, the patient's blood flow path, indicated with arrows "B" extends through the heat exchanger 240 after flowing through the de-aering region 250, prior to interfacing with the first oxygenation zone 222 of the membrane assembly 214.

The heat exchanger 240 is fluidly open to the membrane assembly 214 concentrically disposed around the heat exchanger 240. After contacting the heat exchanger 240, the blood then flows radially outward to the first zone 222 of the membrane assembly 214. The first zone 222 is fluidly open to the second zone 224. The first zone can be configured to be fluidly coupled to an oxygen source to supply oxygen to an interior of the plurality of gas exchange elements. A negative pressure source can be fluidly coupled to the plurality of gas exchange elements to pull gaseous micro emboli (GME) from the plurality of gas exchange elements in the second zone. The negative pressure source can be used to apply suction to remove gaseous micro emboli from blood circulated through the apparatus. In some embodiments, the first zone 222 has an enlarged volume as compared to that of the second zone 224. The blood outlet is formed by or assembled to the central portion and is fluidly open to the gaseous emboli removal zone. In this regard, in some embodiments, the blood outlet extends radially relative to the central axis "C".

As indicated by arrows "B" in FIGS. 2A and 2B, the blood flow path enters the oxygenator apparatus tangentially, then circularly and longitudinally along the core 236, continuing radially through each of the heat exchanger 240 zone, the first (oxygenation) zone 222, and the second (GME removal) zone 224. As illustrated in FIG. 2A, separate gas flow pathways are defined by the separate zones formed by the fibers of the heat exchanger 240 with a heat transfer pathway (indicated with arrows "H"), the first plurality of gas exchange elements 220a in the first zone 222 with an oxygenation pathway (indicated with arrows "O"), and the second plurality of gas exchange elements 220b in the second zone 224 with negative pressure facilitating GME removal (indicated with arrows "G"). The apparatus 200 can thus perform gross air removal, temperature control, oxygenation, and gaseous micro emboli (GME) removal of the patient's blood (as part of an extracorporeal blood circuit) with efficiency and effectiveness in each component or zone.

Figure 3:
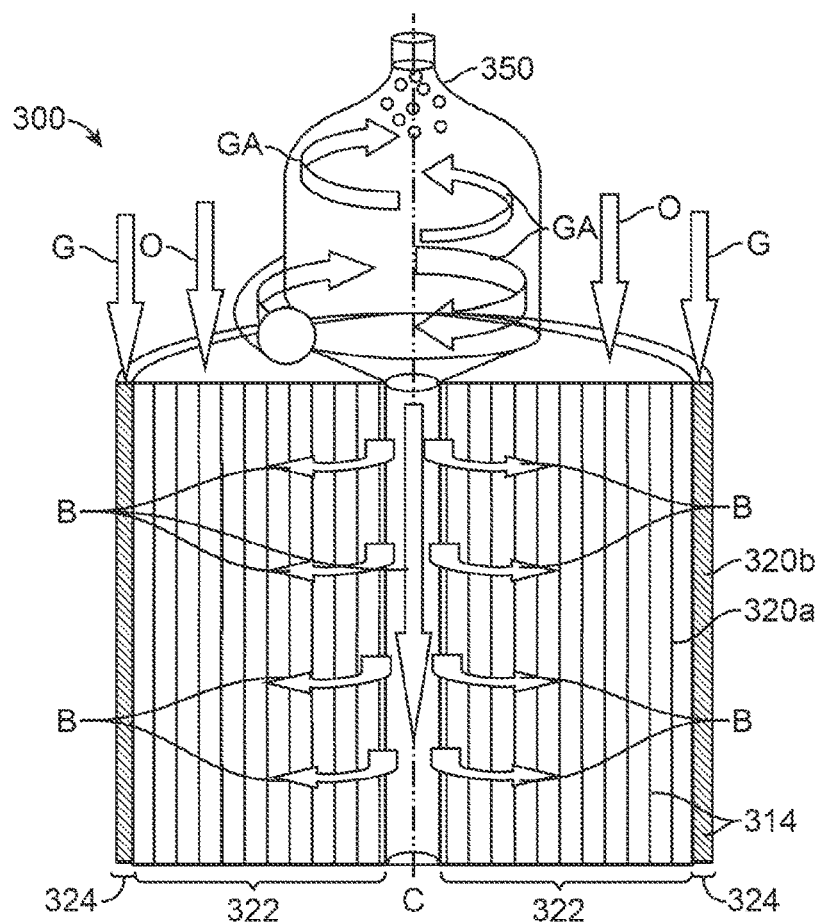
FIG. 3 a schematic cross-sectional view of another oxygenator apparatus in accordance with aspects of the present disclosure.

FIG. 3 illustrates an example embodiment of an oxygenator apparatus 300 including a de-aering region or bubble trap 350 and a membrane assembly 314 including first and second plurality of gas exchange elements 320a, 320b. In one embodiment, blood is directed from an inlet (not shown) tangentially into the de-aering region 350. Gross air removal from the blood, indicated by arrows "GA" occurs within the de-aering region 350 prior to interaction of the blood with the oxygenating and GME removing membrane assembly 314. A blood flow path, indicated with arrows "B", continues from the de-aering region 350 and longitudinally along the central axis "C" to flow radially through the first zone 322 and then the second zone 324. As described above with respect to apparatuses 100 and 200, separate gas flow pathways are defined by the separate zones formed by the fibers of the first plurality of gas exchange elements 320a with an oxygenation pathway (indicated with arrows "O"), and the second plurality of gas exchange elements 320b with negative pressure facilitating GME removal (indicated with arrows "G").

Figure 4:
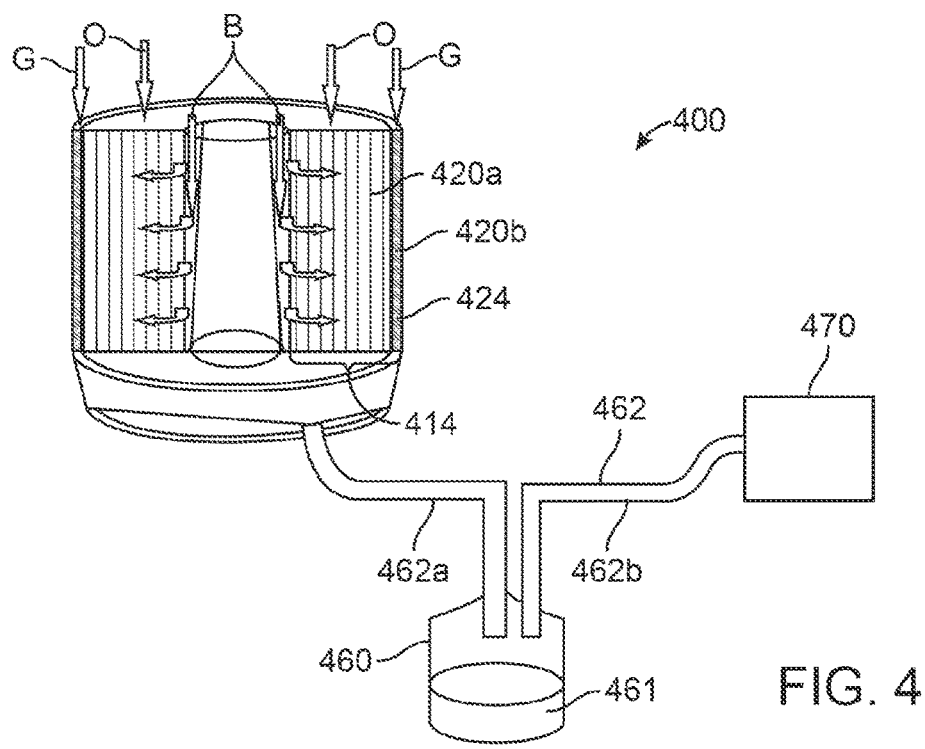
FIG. 4 a schematic cross-sectional view of another oxygenator apparatus in accordance with aspects of the present disclosure.

As illustrated in the example embodiment of FIG. 4, a fluid collection device 460 can be disposed along a vacuum line 462, between an outlet port of the oxygenator apparatus 400 and a negative pressure source 470. The fluid collection device 460 can be included with any of the apparatuses 100, 200, or 300. The fluid collection device 460 can be used to trap fluids 461, such as blood plasma liquids, that may be pulled from the blood through the fiber walls of the second plurality of gas exchange elements 420b in a second zone of a membrane assembly 414 by the negative pressure source 470. The fluid collection device 460 can be a disposable container removably connected to the vacuum line. The vacuum line 462 can include an air gap at the fluid collection device 460, essentially separating the vacuum line 462 into first and second portions 462a, 462b to allow fluids (e.g., plasma) to enter the fluid collection device 460 and gases to be suctioned past the fluid collection device 460 by the negative pressure source 470.

Figure 5A:
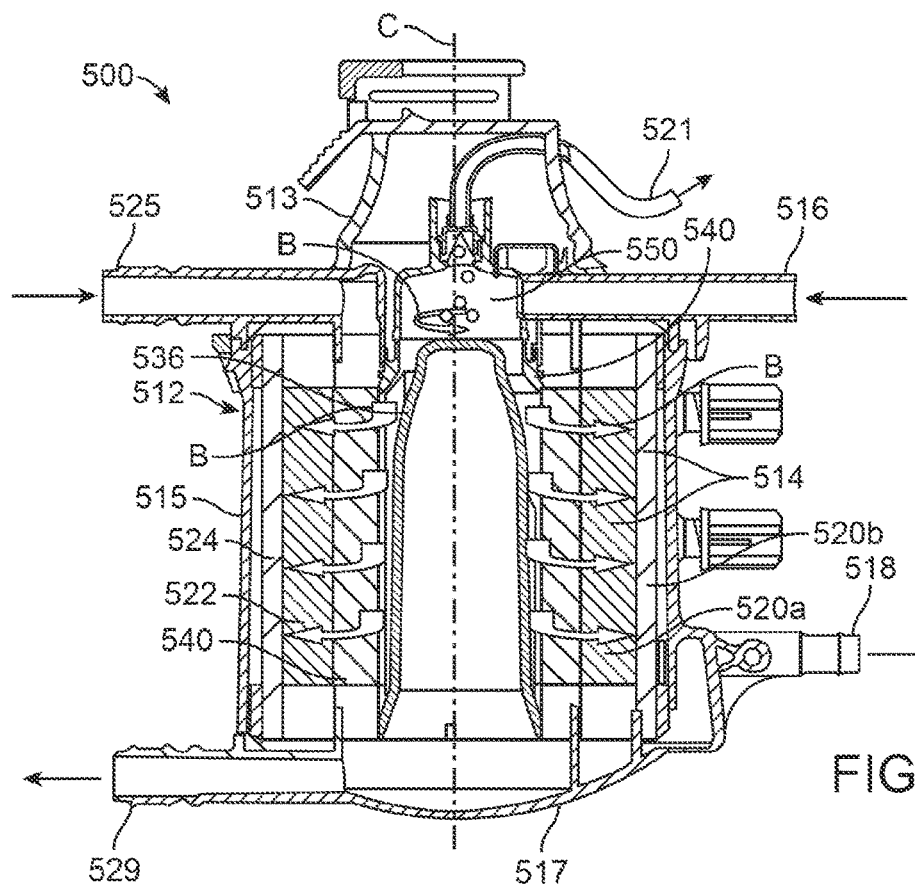
FIGS. 5A and 5B are cross-sectional views of an oxygenator apparatus in accordance with aspects of the present disclosure.
Figure 5B:
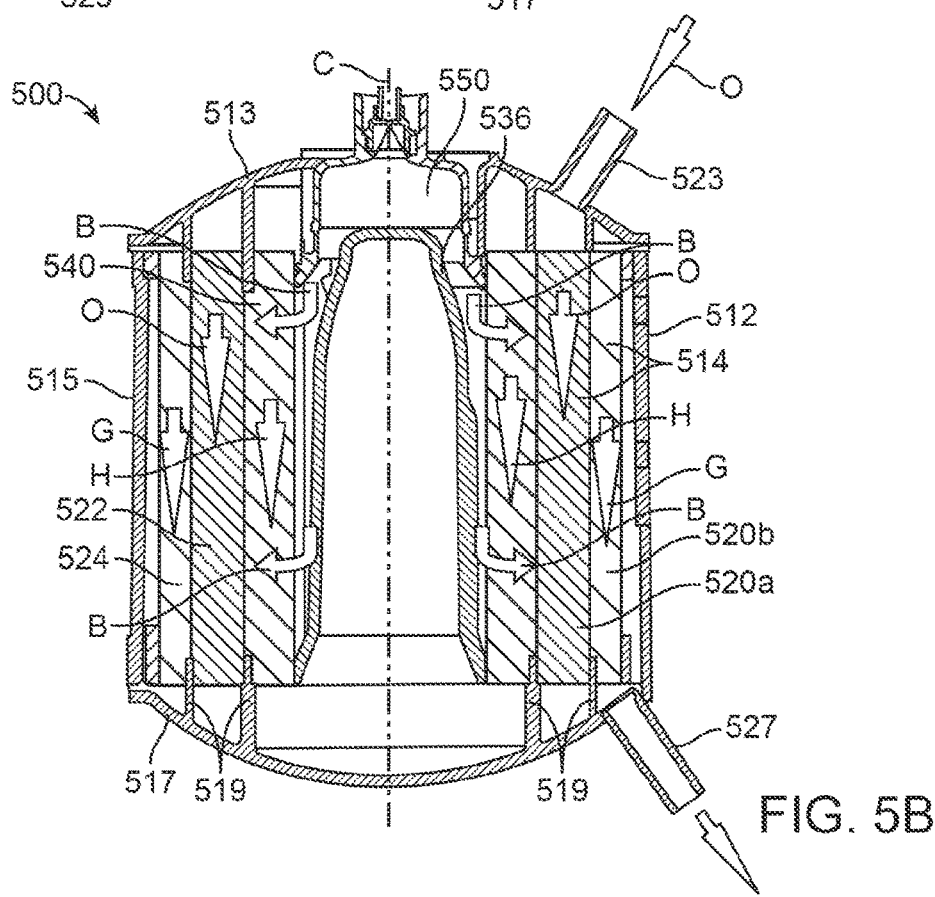

FIG. 5 illustrates an example cross-sectional view of an oxygenation assembly 500 including a housing 512. The housing 512 can include various components separately formed and subsequently assembled to one another, such as a first or upper end cap 513, a central portion or chamber 515, and a second or lower end cap 517. The end caps 513, 517 are configured for assembly to opposing ends of the central portion 515. In other constructions, the central portion 515 is integrally formed with one or both of the end caps 513, 517. The housing 512 can be made of a transparent medical grade material, such as transparent polycarbonate, so that a user is able to observe the flow of blood through the apparatus 500.

The housing 512 includes a blood inlet 516, a blood outlet 518, and a blood flow path, indicated by arrows "B", from the blood inlet 516 to the blood outlet 518. In one embodiment, the blood inlet 516 is arranged to direct incoming blood into the housing 512 at a first, or proximal, end and toward the central axis "C" of the housing 512. The blood inlet 516 can be integrally formed by the first end cap 513. Alternatively, the blood inlet 516 can be separately formed, and subsequently assembled to, the first end cap 513. In one embodiment, the blood outlet 518 is disposed radially outward from the blood inlet 516. In some embodiments, when a de-aering region 550 is included, the blood inlet 516 is fluidly open to a first chamber including the de-aering region 550. To this end, the blood inlet 516 is arranged such that the opening opens tangentially along a horizontal plane (i.e., perpendicular to the central axis "C") into the de-aering region 550. With this construction, the blood inlet 516 directs incoming blood substantially tangentially into the de-aering region 550 to produce a rotational flow along a side wall, and in particular a vortex flow. An air purge port 521 formed at or by the top wall being fluidly open to the de-aering region 550.

The central portion 515 of the housing 512 has a substantially cylindrical shape, and when assembled to the first and second end caps 513, 517, generally defines the chamber 515 with a central axis "C" extending longitudinally therethrough. In some embodiments, a volume displacing core 536 is disposed along the central axis "C" and a first (oxygenation) zone 522 and a second (gaseous micro emboli removal) zone 524 of a oxygenating membrane assembly 514 can be disposed concentrically around the core 536. In one embodiment, a heat exchanger 540 is included between the core 536 and first zone 522 to effectuate temperature control of the blood. A heat exchange medium flow path, indicated with arrows "H", can be established from a heat exchanger inlet port 525, through the fibers of the heat exchanger 540, and to a heat exchanger outlet port 529. The blood outlet 518 is positioned downstream of the heat exchanger 540 and the oxygenating membrane assembly 514. A first plurality of gas exchange elements 520a in the first zone 522 can be fluidly connected to a supply of an oxygen containing medium at an oxygen inlet port 523. Oxygen medium can be provided to the blood flow through the interior lumens of the first plurality of gas exchange elements 520a, indicated by arrows "O", and carbon dioxide removed from the blood through the interior lumens of the first plurality of gas exchange elements 520a to exit the apparatus 500, such as to be vented to the atmosphere (not shown). The second plurality of gaseous exchange elements 520b in the second zone 524 are fluidly coupled to a negative pressure source at a suction, or negative pressure, outlet 527. The outlet 527 illustrated at the second end cap 517 would be useful, for example, with embodiments including the oxygen flow "O" and the GME flow "G" are generally parallel flows in the same direction, as shown (also see, e.g., FIG. 1A). Alternatively, the suction outlet 527 may be disposed at the first end cap 513 (not shown), with embodiments including the oxygen flow "O" transferred from the first plurality of gas exchange elements 520a to the second plurality of gas exchange elements 520b at the second end cap 517 (distal end) and the GME flow "G" through the second plurality of gas exchange elements 520b is in a generally opposite direction to the oxygen flow "O" (e.g., FIG. 1B).

The housing 512 can form or carry other ports in addition to those described above. The second end cap 517, or the distal end of the housing 512, can include a divider 519 for fluidly separating, or isolating, a distal end of the plurality of gas exchange elements 520 between the first (oxygenation) zone 522 and the second (gaseous micro emboli removal) zone 524. In some embodiments, the plurality of gas exchange elements 520 can be fluidly separated at the between the first (oxygenation) zone 522 and the second (gaseous micro emboli removal) zone 524 at the first end cap 513, or the proximal end of the housing 512, with a divider 519. The dividers 519 in the first and/or second end caps 513, 517 provide separation between the first zone 522 and second zone 524, with a suction outlet included at the second zone 524. The second zone 524 is fluidly open to the blood outlet 518 and the suction outlet 527 to maximize GME removal from the blood. Dividers 519 can also be included at one or both of first and second end caps 513, 517 between the heat exchanger 540 and the first zone 522. Dividers 519 can be ring shaped or other suitable shape.

Figure 6:
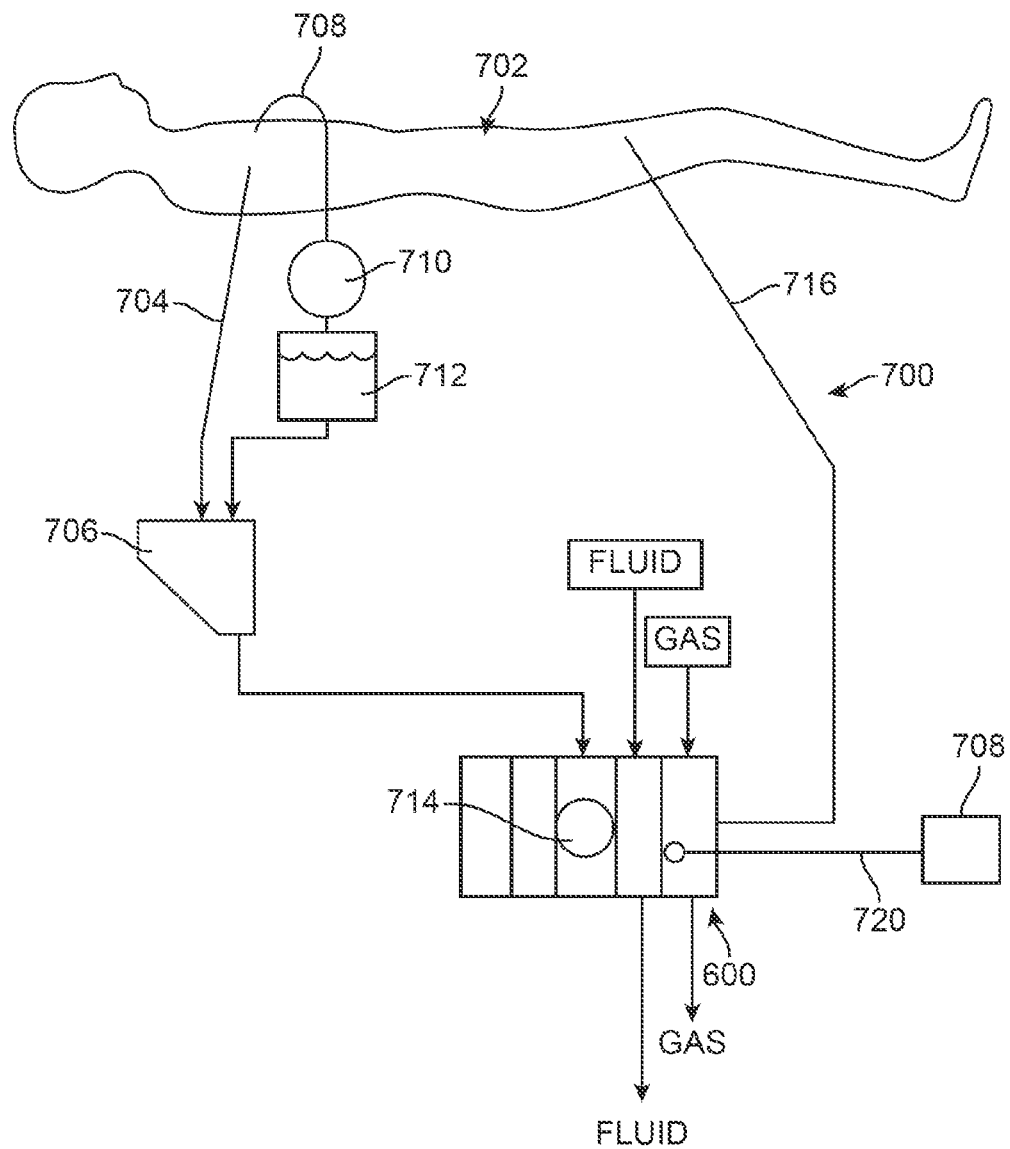
FIG. 6 is a schematic illustration of an extracorporeal circuit including an oxygenator apparatus of the pending disclosure.

FIG. 6 is a schematic illustration of an example extracorporeal circuit 700 including an oxygenator apparatus 600 of the pending disclosure. The oxygenator apparatus 600 is akin to any of the oxygenator apparatuses 100, 200, 300, 400, 500. The circuit 700 generally draws blood of a patient 702 during cardiovascular surgery through venous line 704. Venous blood drawn from the patient 702 is discharged into a venous reservoir 706. Cardiotomy blood and surgical field debris are aspirated by a suction device 708 and are pump by a pump 710 into a cardiotomy reservoir 712. Once defoamed and filtered, the cardiotomy blood is also discharged into the venous reservoir 706. Alternatively, the function of the cardiotomy reservoir 712 may be integrated into the venous reservoir 706. In the venous reservoir 706, air entrapped in the venous blood rises to the surface of the blood and is vented to the atmosphere.

A pump 714 draws blood from the venous reservoir 706 and pumps it through the apparatus 600. As described above, the blood may be de-aerated, temperature controlled, oxygenated, and GME filtered by the oxygenator apparatus 600, and then returned to the patient 702 via an arterial line 716. A suction line 720 can connect to the suction device, or negative pressure source, 708 to apply suction to and pull GME from the blood in the oxygenator apparatus 600 prior to the blood being returned to the patient 702 via the arterial line 716.

Although the present disclosure has been described with reference to preferred embodiments, workers skilled in the art will recognize that changes can be made in form and detail without departing from the spirit and scope of the present disclosure.

What is claimed is:

1. A blood oxygenator comprising:
   a housing defining a volume within the housing, a plurality of zones dividing the volume,
   a blood inlet, a blood outlet, and a blood flow path through the plurality of zones from the blood inlet to the blood outlet;
   a membrane assembly disposed within the housing, the membrane assembly including a first plurality of gas exchange elements disposed in a first zone of the housing and a second plurality of gas exchange elements disposed in a second zone of the housing, one of the zones arranged around another zone, the first zone and the second zone being fluidly open to one another along a body of the plurality of gas exchange elements and fluidly separated from one another along a distal end of the housing, each of the plurality of gas exchange elements including an interior gas side and an exterior blood side;
   in which the first zone may be fluidly connected to one of oxygen and negative pressure within the interior gas side of the first plurality of gas exchange elements of the first zone and the second zone may be fluidly connected to another of oxygen and negative pressure applied to the interior side of the second plurality of gas exchange elements in the second zone, and in which the blood flow path is sequential through the first zone and second zones to add oxygen to the blood and remove carbon dioxide from the blood at one of the first and second plurality of gas exchange elements, and to separate gaseous micro emboli from the blood at another of the first and second plurality of gas exchange elements.

2. The oxygenator of claim 1, in which the distal end of the housing includes a divider for fluidly separating the distal end of one of the plurality of gas exchange elements between different zones.

3. The oxygenator of claim 2, in which the distal end of the housing includes an outlet port for venting one of the plurality of gas exchange elements to atmosphere.

4. The oxygenator of claim 1, in which the housing has a central axis and each of the first and second plurality of gas exchange elements are disposed concentrically around the central axis.

5. The oxygenator of claim 4, in which the first and second plurality of gas exchange elements are each disposed helically around the central axis.

6. The oxygenator of claim 5, in which the plurality of gas exchange elements is disposed helically around the central axis in a first direction in a first zone and the plurality of filter elements is disposed helically in a second direction in the second zone.

7. The oxygenator of claim 1, further comprising a heat exchanger within the housing.

8. The oxygenator of claim 7, in which the membrane assembly is disposed around the heat exchanger.

9. The oxygenator of claim 1, further comprising a volume displacing core within the housing, the core configured to receive blood from a patient through the blood inlet.

10. The oxygenator of claim 9, in which the membrane assembly is disposed around the volume displacing core.

11. The oxygenator of claim 1, further comprising a de-aering region to remove gross air from the blood along the blood flow path prior to flow through the first zone.

12. A method of oxygenating blood and removing gaseous micro emboli from the blood, comprising:
   delivering the blood from a patient to an oxygenator, the oxygenator comprising:
   a housing defining a volume within the housing, a plurality of zones dividing the volume, a blood inlet, a blood outlet, and a blood flow path through the plurality of zones from the blood inlet to the blood outlet;
   a membrane assembly disposed within the housing, the membrane assembly including a first plurality of gas exchange elements disposed in a first zone of the housing and a second plurality of gas exchange elements disposed in a second zone of the housing, one of the zones arranged around another zone, the first zone and the second zone being fluidly open to one another along a body of the plurality of gas exchange elements and fluidly separated from one another along a distal end of the housing, each of the plurality of gas exchange elements including an interior gas side and an exterior blood side;
   fluidly coupling the interior lumens of the plurality of gas exchange elements in the first zone to one of an oxygenation source and a negative pressure source, and fluidly coupling the interior lumens of the plurality of gas exchange elements in the second zone to another of an oxygenation source and a negative pressure source; and
   directing blood from the blood inlet to the blood outlet along the blood flow path to add oxygen to the blood and remove carbon dioxide from the blood at one of the first and second plurality of gas exchange elements, and to separate gaseous micro emboli from the blood at another of the first and second plurality of gas exchange elements.

13. The method of claim 12, in which separation of gaseous micro emboli from the blood in the second zone is subsequent to adding oxygen to the blood in the first zone.

14. The method of claim 12, further comprising removing gross air from the blood along the blood flow path prior to one of the first and second zones.

15. The method of claim 12, further comprising transferring heat to the blood within the oxygenator by a heat exchanger prior to oxygenating the blood.

16. The method of claim 12, further comprising collecting liquids from the interior lumens of the plurality of gas exchange elements fluidly coupled to the negative pressure source.

17. A system for treating blood in an extracorporeal circuit, the system comprising:
   an oxygenator, comprising a housing defining a volume within the housing, a plurality of zones dividing the volume, a blood inlet, a blood outlet, and a blood flow path from the blood inlet to the blood outlet; and a membrane assembly disposed within the housing, the membrane assembly including a first plurality of gas exchange elements disposed in a first zone of the housing and a second plurality of gas exchange elements disposed in a second zone of the housing, the second zone arranged around the first zone, the first zone and the second zone being fluidly open to one another along a body of the plurality of gas exchange elements and fluidly separated from one another along a distal end of the housing, each of the plurality of gas exchange elements including an interior gas side and an exterior blood side;
   an oxygen source fluidly coupled to the first plurality of gas exchange elements at the first zone to provide oxygen to interior lumens of the first plurality of gas exchange elements; and
   a negative pressure source fluidly coupled to the second plurality of gas exchange elements at the second zone, the negative pressure source to provide suction to interior lumens of the second plurality of gas exchange elements, in which the system adds oxygen to the blood and removes carbon dioxide from the blood at the first plurality of gas exchange elements, and separates gaseous micro emboli from the blood at the second plurality of gas exchange elements.

* * * * *